United States Patent [19]

Waller

[11] Patent Number: 5,369,395
[45] Date of Patent: Nov. 29, 1994

[54] DIFFERENTIAL FLOAT MEANS AND SENSOR MEANS INCORPORATING SAME

[75] Inventor: Clive G. Waller, Geraldton, Australia

[73] Assignee: Refrigerant Monitoring Systems Pty Ltd., Australia

[21] Appl. No.: 971,988
[22] PCT Filed: Aug. 23, 1991
[86] PCT No.: PCT/AU91/00386
§ 371 Date: Feb. 19, 1993
§ 102(e) Date: Feb. 19, 1993
[87] PCT Pub. No.: WO92/03718
PCT Pub. Date: Mar. 5, 1992

[30] Foreign Application Priority Data

Aug. 23, 1990 [AU] Australia .................. PK1882

[51] Int. Cl.5 .............................................. G08B 21/00
[52] U.S. Cl. .................................... 340/603; 340/625; 62/129; 73/305
[58] Field of Search ............... 340/603, 618, 625, 632; 62/129; 73/305, 307, 309, 317, 323, 308

[56] References Cited

U.S. PATENT DOCUMENTS 3,365,899  1/1968  Cuny et al. .
4,138,879  2/1979  Liebermann .................. 62/129 X
4,876,888  10/1989  Ricketts et al. .

FOREIGN PATENT DOCUMENTS

46459/79  6/1981  Australia .
66552/81  8/1981  Australia .
68405/90  7/1991  Australia .
1277972  6/1972  United Kingdom .

OTHER PUBLICATIONS

Patent Abstracts of Japan, P-979, p. 101, JP,A,-1-242938 (Nisshin Steel Co Ltd) 27 Sep. 1989.
Derwent Abstract Accesion No. 20943A/11, class H03, SU,A, 556334 (Shorokhov) 23 May 1977.

Primary Examiner—Jeffery A. Hofsass
Attorney, Agent, or Firm—Larson and Taylor

[57] ABSTRACT

A sensor (1) is provided for sensing the entrainment of a fluid of low specific gravity in a fluid of higher specific gravity, particularly the entrainment of refrigerant gas in refrigerant liquid. The sensor (1) is typically installed into a higher pressure liquid supply line (24) of a refrigeration system (26). The sensor (1) has a differential float (16) including a float member (54) pivoted about a pivot (56) in a chamber (14) coupled to the supply line (24). The float member (54) has a specific gravity greater than the specific gravity of both of the fluids in which it operates. However, the location of the pivot (56) intermediate of the length of the float member (54) gives a net specific gravity for the differential float (16) which is less than the specific gravity of one of the fluids. Hence, the differential float (16) can withstand a high pressure operation, say at 2MPa, and can operate as a float for detecting the presence or absence of the fluid of lower specific gravity in the fluid of high specific gravity. The differential float (16) can also be used as gauge snubber (20) or to replace refrigerant capillary control tubes.

17 Claims, 4 Drawing Sheets

DIFFERENTIAL FLOAT MEANS AND SENSOR MEANS INCORPORATING SAME

FIELD OF THE INVENTION

The present invention relates to a differential float means and sensor incorporating same. The differential float means is particularly, although not exclusively, envisaged for use in detecting the entrainment of a gas in a liquid. The sensor means is particularly, although not exclusively, envisaged for use in detecting excess refrigerant vapour entrained in refrigerant liquid in a refrigeration system.

The present invention will hereinafter be described with particular reference to use in refrigeration systems although it is of general applicability. For example, the invention could be used to detect the entrainment of a fluid, having a given specific gravity, in another fluid having a different specific gravity.

DISCUSSION OF PRIOR ART

When there is a loss of refrigerant from a refrigeration system refrigerant vapour becomes entrained in refrigerant liquid in both low pressure and high pressure lines in the refrigeration system. This greatly reduces the efficiency and effectiveness in cooling of the refrigeration system.

It is known to provide refrigeration cooling systems with a sight glass S (see FIG. 1) in a high pressure liquid supply (hereinafter referred to as the high pressure line) line so that a technician may observe the occurrence of refrigerant vapour entrained in the refrigerant liquid immediately up stream from a refrigerant expansion device. A disadvantage of the use of a sight glass S is that the entrained vapour can only be detected when inspected. An amount of refrigerant must be lost before the entrained vapour can be observed by a technician inspecting the refrigerant through the sight glass S. Also, due to the time between inspections, considerable amounts of refrigerant may leak from the refrigerant system (thus causing vapour to be circulated with the refrigerant liquid) before the technician observes vapour bubbles in the refrigerant.

It is also known to install a liquid level detector in a storage reservoir R (see FIG. 1) of the refrigeration system to monitor the proper functioning of the system. The detector is set to trigger an alarm in the event that the liquid level falls below a predetermined level. The detector includes a float switch for detection of changes in liquid level about the predetermined level. The float switch is a conventional nature designed to operate under the relatively high pressure conditions existing in the storage reservoir R.

There are some difficulties in installing and operating conventional float switches in the high pressure line. This is because for conventional float switches to operate they must comprise elements which are capable of floating in the liquid, whose level they are to detect, and capable of withstanding relatively high pressures. Hence, the specific gravity of the float switch must be less than the specific gravity of the refrigerant liquid yet, at the same time, be strong enough so as not to collapse under the pressure of the surrounding fluid. To this end the floats generally have relatively thick walls which are capable of withstanding the pressures experienced in the high pressure line, such as, for example, about 2 MPa and are relatively large in diameter so as to float in the refrigerant liquid.

A disadvantage of such an arrangement is that further refrigerant must be added to the storage reservoir to enable proper functioning of the relatively large float switch. The cost of adding the extra refrigerant is significant and in the case of horizontally disposed storage reservoirs it is sometimes impractical. Another disadvantage is that such float switches cannot detect low levels of refrigerant liquid in the high pressure line and thus can not detect vapour entrained in the refrigerant liquid in the high pressure line.

Location of the float switch in the reservoir has the added disadvantage that false level sensing of the float switch can occur where the refrigerant liquid is spinning as in a whirlpool (which is not uncommon). In such a case, the float switch may not show the actual amount of refrigerant liquid depending on which part of the whirlpool the float switch is located. Further, some refrigeration systems do not have reservoirs. Still further, due to the size of such float switches, it is not practical to install them in the high pressure line.

Thus, in both of the above prior art systems there can be significant leakage of refrigerant before such is detected.

The above disadvantages can be overcome by locating a device capable of detecting vapour bubbles in the high pressure line. In the present invention this is achieved with a sensor incorporating a differential float means capable of operating at substantially elevated pressures, such as, for example, 2 MPa as is the case in conventional refrigeration systems.

In accordance with one aspect of the present invention there is provided a differential float means for detecting the entrainment of a first fluid in a second fluid, the second fluid having a greater specific gravity than the first fluid the differential float means having:

a float member shaped for location and movement within a chamber, the float member having a specific gravity greater than those of the first and second fluids, whereby, in use, the float member can be moved between two locations under the influence of the fluids depending upon the buoying force exerted by the relative quantities of the fluids present for sensing the entrainment of the first fluid in the second fluid.

In accordance with another aspect of the present invention there is provided a sensor means for sensing the entrainment of a first fluid in a second fluid, the second fluid having a greater specific gravity than the first fluid, the sensing means comprising:

a chamber disposed upwardly for communication with the fluids; and, a differential float means having a float member shaped for location and movement within the chamber the float member having a specific gravity greater than those of the first and second fluids, whereby, in use, the first fluid can displace the second fluid from the chamber to inhibit buoying of the float member so that the float member is moved under the influence of the fluid between two locations depending upon the buoying force exerted by the relative quantities of the fluids present for sensing the entrainment of the first fluid in the second fluid.

Typically, an alarm means is located for actuation by the differential float means upon movement% between the two locations within the chamber.

Preferably, the float member is solid or substantially solid so as to withstand pressures in excess of atmospheric pressure, and to be relatively small. It is the location of the pivot intermediate the length of the float member that allows the float element to operate as a fluid level float even though its actual specific gravity is greater than that of the fluids. However, the nett specific gravity of the float means due to the pivoting forces operating on the float member at each side of the pivot is less than the specific gravity of one of the fluids but greater than the specific gravity of the other fluid. Thus, the float means pivots to a floated position in the presence of one of the fluids and pivots to a non-floated position upon the introduction of more than a predetermined quantity of the other fluid.

Typically, the second fluid has a relatively high specific gravity, such as a liquid, and the first fluid has a relatively low specific gravity, such as a gas, although both fluids could be liquids. The predetermined quantity representing a maximum acceptable amount of the gas which may be entrained in the liquid.

Typically, the float member has a magnet located in one of its ends for actuation of a reed switch of the alarm means.

Preferably, the chamber has an inlet connected into a fluid line to allow some fluid to flow out of the fluid line into the chamber.

Typically, the chamber also has a bleed tube to allow a relatively slow flow of the fluids out of the chamber back to the fluid line. The rate of flow of fluid in the bleed tube is to be slow compared to the typical rate of collection of gas in the chamber at the maximum acceptable amount of the gas entrained in the liquid. This may be important where the gas is soluble in the liquid at slightly elevated temperatures, because the flow out of the chamber has the effect of avoiding temperature build up of the fluids in the chamber.

Preferably, the alarm means includes a delay means to avoid triggering the alarm by short term occurrences of excess quantities of the gas.

BRIEF DESCRIPTION OF THE DRAWINGS

One embodiment, being an example, of the present invention will now be described with reference to accompanying drawings, in which.

DESCRIPTION OF THE PREFERRED EMBODIMENT

Figure 2:
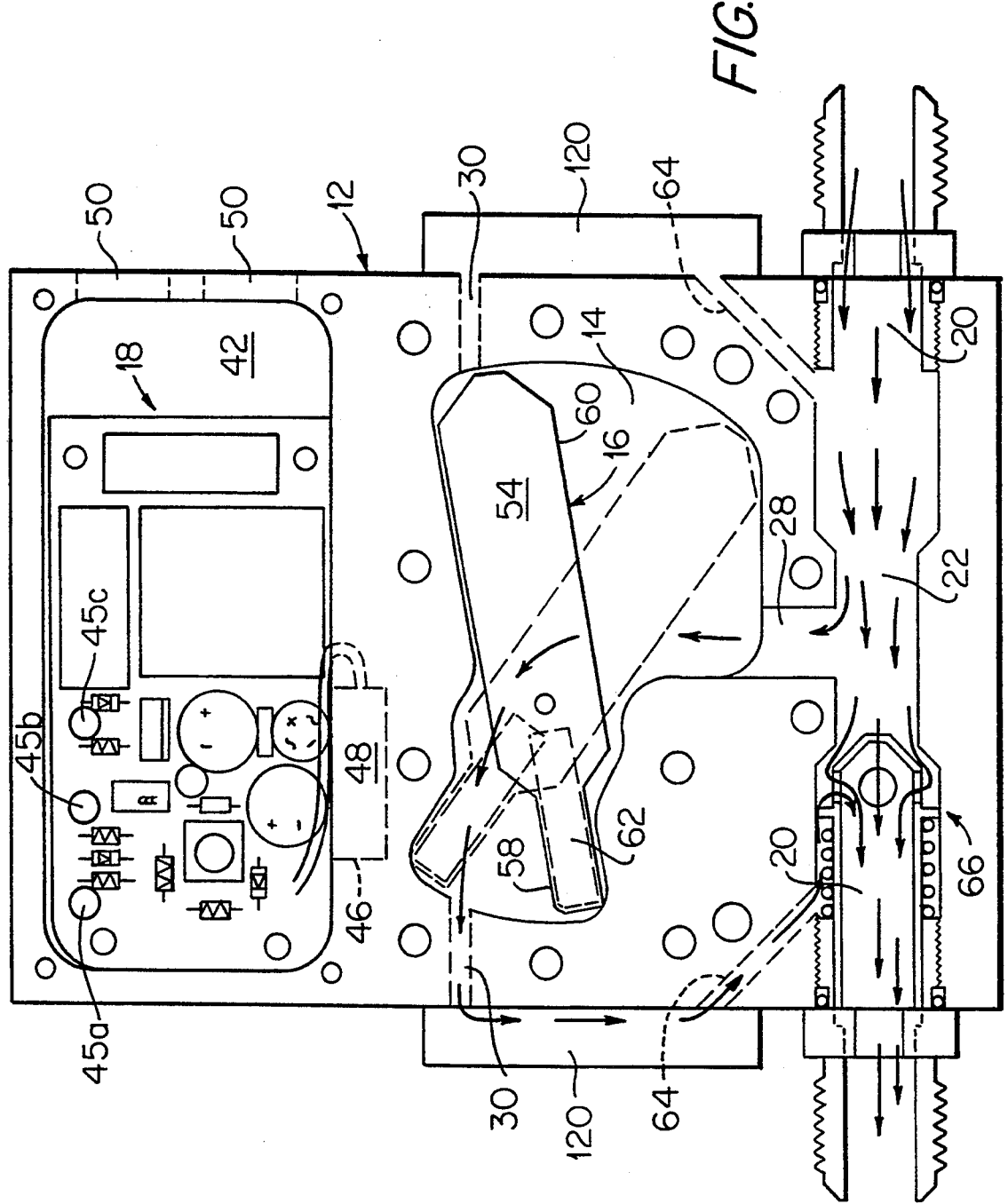
FIG. 2 is a schematic plan view of the sensor means of FIG. 1.
Figure 3:
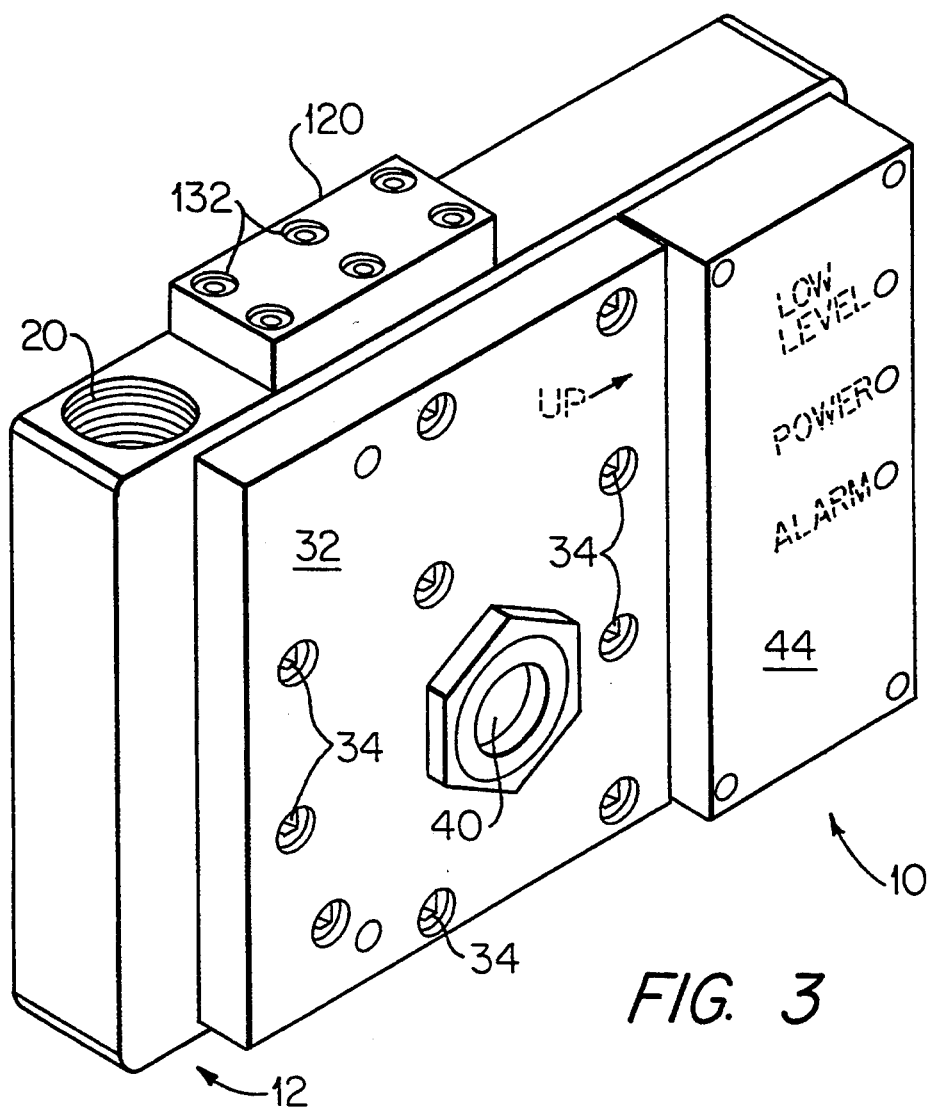
FIG. 3 is a perspective view seen from above of the sensor means of FIG. 1.
Figure 5A:
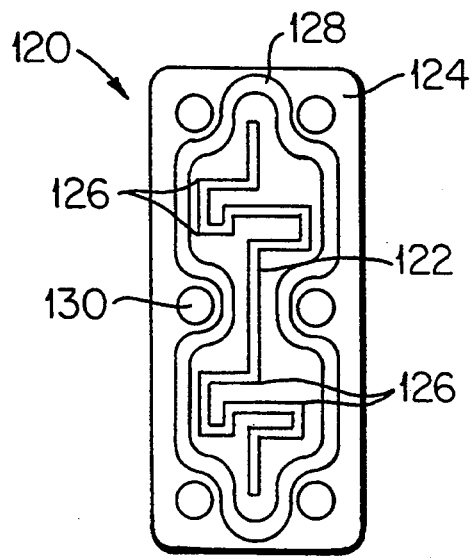
Figure 5B:
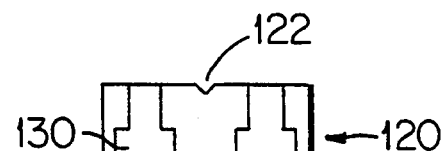
Figure 5C:
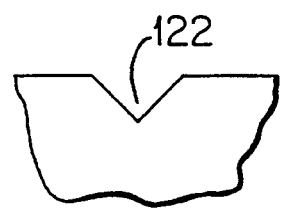

In FIGS. 2 and 3 there is shown a sensor 10 comprising a housing 12 defining a chamber 14, a differential float 16 positioned within the chamber and an alarm 18 for actuation by the differential float 16.

Figure 1:
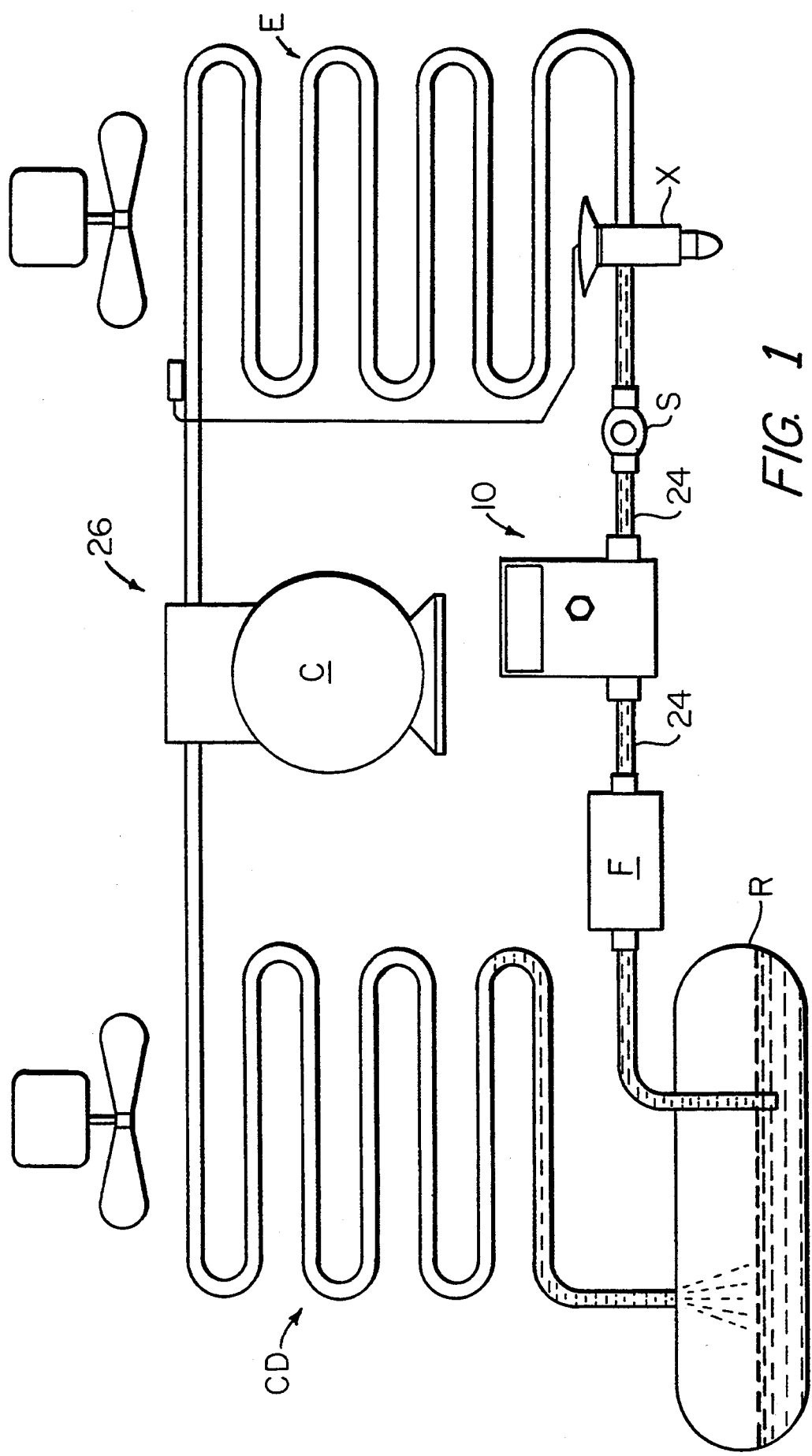
FIG. 1 is schematic representation of a conventional refrigeration system having a sensor means incorporating a differential float means installed in its high pressure liquid supply line.

The housing 12 is made of non-ferrous metal material, such as, for example, aluminium. The housing 12 also comprises two ports 20 coupled together by a conduit 22. Each portion 20 is provided with a thread for connection to a fluid line 24 of a refrigeration system 26 as shown in FIG. 1. The refrigeration system 26 includes a sight glass S, a refrigerant expansion device X located downstream thereof and connected to an evaporator E for absorbing heat from a cooling box. A compressor C receives cool gas from the evaporator E and produces high pressure gas which is liquefied by a condenser CD and stored in a storage reservoir R for supply into the high pressure line 24 through a filter dryer F and back through the sight glass S through the sensor 10.

The housing 12 also comprises a conduit 28 connecting the conduit 22 to the chamber 14. The conduit 28 acts as an inlet to the chamber 14. The chamber 14 has two outlets 30 disposed to communicate with gas that collects within the chamber 14 as described hereinafter. Particularly as shown in FIG. 3 the housing 12 has a cover/32 fixed to it with bolts 34 to seal off the chamber 14. Provided in the cover 32 is a groove disposed to extend continuously about the chamber 32. The groove receives an O-ring.

A conventional sight glass 40 is threaded into a hole located in the cover 32 to allow for visual inspection of the interior of the chamber 14. The sight glass 40 is typically also provided with a conventional moisture indicator. As shown in FIG. 2, the housing also comprises a recess 42 dimensioned to receive the alarm 18. A further cover 44 (see FIG. 3) is provided to seal off the recess 42. The cover 44 is provided with three holes to receive status LEDS 45a, 45b, 45c of the alarm 18. The recess 42 includes a cavity 46 extending towards the chamber 14. The cavity 46 is dimensioned to receive a reed switch 48 of the alarm 18. The housing 12 also has two access ports 50 each provided with a gland (not shown) for receipt of electrical cabling between the alarm 18 and an external alarm or monitoring system as described hereinafter.

As shown in FIG. 2, the differential float 16 comprises an elongate float member 54, which in the present embodiment is substantially cricket bat-shaped and is not itself capable of floating in the liquid in which it is to operate. The float 16 also has a pivot 56 located intermediate of the length of the float member 54. The pivot 56 is located closer to a thin end 58 than a thick end 60 of the float member 54. A reed magnet 62 is formed into the float member 54 at the thin end 58. The pivot 56 is so arranged that in air the float member 54 pivots under the action of the force of gravity so that the thick end 60 is lower most. The reed magnet 62 and the thin end 58 act as a counter balance for the float member 54. The effect of the reed magnet 62 and the thin end 58 is that introduction of liquid refrigerant into the chamber 14 produces an upward pivoting force against the thick end 60 which tends to pivot the float member 54 to a first substantially horizontal position shown in solid line. The upward buoyant force is assisted by the counter balancing force created by the force of the weight of reed magnet 62 and the thin end 58 of the float member 54. These two forces are counteracted by a counter pivoting force produced by the force of the weight of the thick end 60 of the float member 54. The net result is that by suitable placement of the pivot 56 the float member 54 can be made to pivot to the first substantially horizontal position when liquid is present in the chamber 14, and to pivot to a second downwardly disposed position, shown in phantom, when the chamber 14 is substantially filled with gas or contains a quantity of gas in excess of a predetermined quantity.

Preferably, the thin end 58 has a specific gravity substantially greater than the thick end 60 for defecting entrainment of a gas in a liquid. For example, the thin end 58 could have a specific gravity of about 7 and the thick end 60 a specific gravity of about 1.2.

The float member 54 is constructed to withstand substantial pressures, such as, for example, 2 MPa or more. This is advantageously achieved by forming the float member 54 from a solid piece of material. In the present embodiment the float member 54 is constructed from Nylon 11, so as to be capable of withstanding substantial pressures and being relatively free from corrosive attack by refrigerant. Thus, the pressure at which the sensor 10 can operate is limited by the strength of the housing 12 and not pressure of which the float member 54 would implode if it were a conventional float member. The float member 54 is also intended to be relatively small, having a length of, for example, about 100 mm. Accordingly, the float member 54 is incapable of itself being buoyed up by liquid refrigerant. However, buoying up of the thick end 60 of the float member 54 is achieved by the counter balancing effect of the reed magnet 62 and the thin end 58 of the float member 54 as described hereinabove.

It is to be noted that the cheer 14 has a shape which is substantially commensurate with the desired pivotable movement of the float member 54 between the first position and the second position. The cheer 14 is shaped to allow the float member 54 to be forced against the upper and lower extents, respectively, of the side walls of the cheer 14 when in the first and the second positions. This has the effect of making the float member 54 relatively stable when in the first and the second positions. Accordingly, the ability of the float member 54 to detect the presence or absence of liquid within the chamber 14 can be made quite accurate.

A conventional restrictor tube may be connected between one of the outlets 30 and one of two return lines 64 leading into the ports 20 so as to allow for relatively slow drainage of the contents of the cheer 14 back into the fluid line 24 downstream of the sensor 10. The restrictor tube be the form of a 600 mm length of 1.8 mm capillary refrigeration tube. The diameter and length of the restrictor tube is chosen so that the rate of flow of fluid through it is very small compared to the rate of flow of fluid into the chamber 14. A check valve 66 is located in the downstream port 20 so as to create a relatively small pressure drop between the upstream portion of the fluid line 24 and the downstream portion of the fluid line 24. This has the effect of acting as a bleed tube for enabling flow of fluid out of the chamber 14 through the restrictor tube to the downstream portion of the fluid line 24. Such flow is necessary to enable removal of refrigerant gas from the chamber 14 at a slow rate after it has collected there. Otherwise, under some conditions the refrigerant gas in the cheer 14 does not reliquefy and this can lead to false triggering of the alarm 18 at start up of the refrigeration system 26 where refrigerant gas ordinarily exists in the high pressure line 24 for several minutes.

Figure 4:
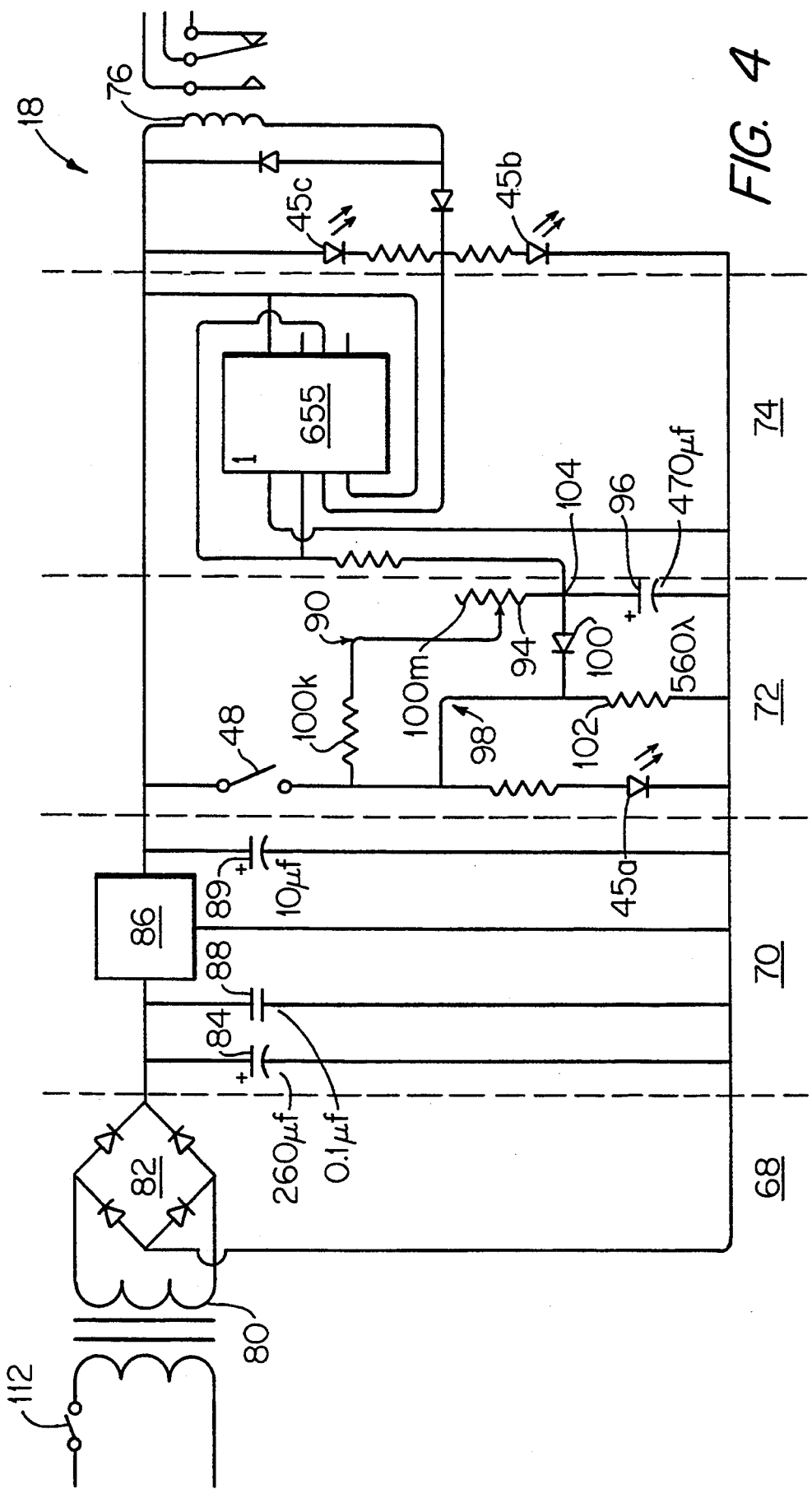
FIG. 4 is a circuit diagram of an alarm means of the sensor means of FIG. 1; and, FIGS. 5a, 5b and 5c are a plan view, a part cross sectional view and an enlarged part cross-sectional view, respectively, of a restrictor of the sensor means.

As shown in FIG. 4, the alarm 18 comprises a power supply 68, a voltage regulator 70, a time delay circuit 72, a threshold detector 74 and a relay 76. The power supply 68 has a transformer 80 connected to a supply of mains electrical power. A full wave bridge rectifier 82 is connected to the secondary of the transformer 80. A DC voltage smoothing capacitor 84 is connected to an output of the bridge rectifier 82 to provide DC power at about 15 volts. The voltage regulator 70 has a series regulator 86, having an output with a voltage regulated to 12 volts. Two AC ripple rejection capacitors 88 and 89 are provided with the series regulator 86. The output of the series regulator 86 is connected via the reed switch 48 to the time delay circuit 72. The time delay circuit 72 has a charging circuit 90 consisting of resistors 92 and 94 and a capacitor 96, typically having values of 100 kohm, 1 Mohm and 470 $\mu$F respectively. The resistor 94 is preferably a variable type resistor so that the charging circuit 90 has a variable time constant of between about 1 minute to about 11 minutes. The time delay circuit 72 also has a discharge circuit 98 consisting of a diode 100 and a resistor 102, the diode 100 being bias towards the resistor 102. The resistor 102 has a value of 560 ohms so that the discharge circuit 98 has a time constant of about 0.15 seconds.

The threshold detector 74 is conveniently embodied in a 555 timer having a trigger pin 2 and a threshold pin 6 tied together and a control voltage pin 5 and a discharge pin 7 floating. The trigger and threshold pins 2 and 6 are connected to a connection 104 between the charging circuit 90 and the discharge circuit 98. The threshold detector 74 is configured so that when the voltage at pins 2 and 6 exceeds two thirds of the voltage from the regulator 86 an output pin 3 of the 555 timer is set active low. The relay 76 is driven by the output pin 3 and is thus activated when the voltage at pins 2 and 6 exceeds two thirds of the supply voltage. The relay 76 has relay contacts wired to activate an external alarm (not shown). The three status LEDs of the alarm 18 are a low level status LED 45a, a power-on status LED 45b and an alarm status LED 45c. The low level LED 45a is wired to be activated immediately upon closure of the reed switch 48. The power-on and alarm LEDs 45b and 45c are both coupled to the output pin 3 of the threshold detector 74 so that only one or the other of the LEDs 45b or 45c is operative at any one time. Hence, during normal operation the power-on LED 45b is activated, but when an alarm condition occurs the alarm LED 45c is activated.

An improved form of restrictor 120 is shown in FIGS. 2 and 3 connected between the outlets 30 and the respective return lines 64. The restrictors 120 are constituted by a groove 122 formed in a block of metal 124. In the present embodiment the groove is "V" shaped, about 0.9 mm deep and has sides sloped at an angle of about 30° to the vertical, that is a contained angle of about 120°. The groove 122 has 16 right angle bends 126 and is about 100 mm in length. Each bend 126 has the effect of increasing the length of that part of the groove 122 by about six times its width. Hence, the bends induce a restriction equivalent to about 100 mm of straight groove. Also, as the flow rate increases, the restriction increases, typically in a squared relation, due to increase in turbulent flow of the refrigerant through the groove 122. Bends of tighter than 90° could be used to eject greater restriction and more bends can be used to achieve greater restriction. The triangular cross section sharp bends 126 in the groove 122 effect a drag and a restriction on flow of refrigerant equivalent to that of a conventional restrictor tube 600 mm long and 1.8 mm in diameter.

Each restrictor 120 also has an "O" ring seal 128 surrounding the groove 122 for sealing the restrictor 120 to the housing 12. The restrictor 120 also has holes 130 for receiving bolts 132 (see FIG. 3) for attaching the restrictor 120 to the housing 12.

The restrictor 120 has the advantage that it relatively short and has a relatively large cross-sectional area. Hence, the likelihood of blockage with foreign matter is small. Also, the groove 122 is very robust and not prone to damage by vibration as microbore tube is.

Since the restrictor 120 is robust, has high restriction and relatively large cross-section it is also suited to use as a gauge snubber where pulsations need to be removed. The restrictor 120 can also be used to replace refrigerant capillary control tubes and the like, requiring high restriction.

The operation of the sensor 10 shown in FIG. 2 will now be described.

In use, the sensor 10 is installed into the fluid line 24 of the refrigeration system 26. The fluid line 24 is a high pressure fluid line carrying liquid refrigerant. The fluid line 24 is coupled by conventional couplings into the ports 20 with the valve 66 in the downstream port 20. The transformer 80 has its primary winding connected to a compressor contact of a relay of the refrigeration system 26 and to a supply of mains power via a switch 112 (see FIG. 4). The switch 112 is typically an existing low pressure switch provided in the refrigeration system 26 to start the compressor C. Relay contacts of the relay 76 are then connected to the external alarm.

Upon start-up of the refrigeration system 26 power is supplied to the power supply 68 which energises the remainder of the alarm 18. At turn-on of the refrigeration system 26, and during the first few minutes after start-up, it is expected that vapour exists in the high pressure line 24, since most of the refrigerant liquid drains into the evaporator E and so the chamber 14 is substantially full of refrigerant vapour and that the float member 54 is in the second position. Accordingly, the reed magnet 62 activates the reed switch 45, which energises the low level LED 45a and commences charging of the capacitor 96. Whilst the capacitor 96 charges the voltage at the pins 2 and 6 of the threshold detector 74 increases. As the voltage increases refrigerant liquid is pumped along the fluid line 24 and begins to fill the chamber 14. During filling the refrigerant vapour in the chamber 14 condenses into the refrigerant liquid. As the refrigerant level within the chamber 14 rises the thick end 60 of the float member 54 pivots upwardly to the first position which pivoting causes deactivation of the reed switch 48. The resistor 94 is adjusted to a valve so that the time constant of the charging circuit 90 is large enough so that the voltage at the pins 2 and 6 of the threshold detector 72 do not reach two thirds of the supply voltage before the refrigeration system 26 reaches proper functioning and fills the chamber 14 with refrigerant liquid. Typically, this time period is between about 1 to 11 minutes depending on the size of the refrigeration system and the quantity of refrigerant used therein.

Upon movement of the float member 54 to the first position the reed switch 48 opens and the low level LED 45a extinguishes and the capacitor 96 begins to discharge through the resistor 102 via the diode 100.

During normal operation the check valve 66 causes a small flow of fluid out of the chamber 14 along the restrictor tube 64 and to the downstream side of the fluid line 24. This flow is preferred so as to avoid heating of the fluid within the chamber 14. Heating of the fluid can lead to vaporisation of the refrigerant liquid into refrigerant vapour which may cause inadvertent triggering of the alarm means 18. During normal operation there may be times when refrigerant vapour is entrained in the refrigerant liquid. When this occurs the vapour rises into the chamber 14 and displaces the refrigerant liquid therein. When a sufficient quantity of the refrigerant liquid is displaced the float member 54 pivots from the first position to the second position and commences charging of the timing capacitor 96. Where the bubbles in the fluid line 24 continue for only a relatively short period of time the capacitor 96 does not charge sufficiently to set of the threshold detector 74.

However, where bubbles occur within the refrigerant liquid for a time exceeding the predetermined time set by the charging circuit 90 the output pin 3 of the threshold detector 74 is set active low which energises the alarm LED 45c, the relay 76 and the external alarm. This simultaneously causes the power-on LED 456 to be extinguished. Once triggered the threshold detector 74 latches and the relay 76 and the external alarm are maintained on. The alarm 10 may be reset by opening of the switch 112.

The sensor 10 shown in FIG. 2 may be used in conjunction with the existing sight glass S used in the refrigeration system 26.

The sensor 10 of the present invention has the advantage that it can detect the level of liquid in the liquid line 24 and provide an alarm in the event that refrigerant gas exists within the fluid line 24 for a period of time exceeding a predetermined time. This allows for early detection of leakage of refrigerant from the refrigeration system 26. This is in contradistinction to prior art sensors which detect the level of refrigerant liquid remaining in a storage reservoir R of the refrigeration system 26. Such prior art sensors do not provide early warning of leakage of refrigerant.

The present invention is also advantageous in that its use of a differential float 16 allows the sensor 10 to be relatively compact and capable of withstanding pressure greatly in excess of atmospheric pressure. Surprisingly, the float member 54 is able to act as a float even though it is of greater specific gravity than the fluids in which it operates.

Modifications and variations such as would be apparent to a skilled addressee are to be deemed within the scope of the present invention. For example, the float member 54 could be constructed to enable detection of one liquid in another liquid, such as, for example, oil in water. For example, the sensor 10 could be adapted for use in airconditioners, such as, for example, automotive and vehicle airconditioners. Also, the contacts of the relay 76 could be coupled to an electrical input port of a computer programmed for managing responses to alarm conditions detected by the alarm 18. Such coupling may be effected remotely by the use of a mode and for other forms of telecommunication.

I claim:

1. A differential float means for detecting the entrainment of a first fluid in a second fluid, the second fluid having a greater specific gravity than the first fluid, the differential float means having:
  a float member shaped for location and movement within a chamber, the float member having a specific gravity greater than those of the first and second fluids,
  whereby, in use, the float member can be moved between two locations under the influence of said fluids depending upon the buoying force exerted by the relative quantities of said fluids present for detecting the entrainment of the first fluid in the second fluid.

2. A differential float means according to claim 1 also having a pivot, the float member being elongate and the pivot being located intermediate the length of the float member such that one end of the float member effects a counterbalance force which partially counterbalances the other end of the float member, whereby, in use, the float member is pivotable between two locations under the influence of said fluids depending upon the buoying force exerted by the relative quantities of the fluids present and whereby the pivoting of the float member depends upon the difference in pivoting force due to the buoying force of said fluids present plus the counterbalance force and the counter pivoting force of the other end of the float member.

3. A differential float means according to claim 2 in which the net specific gravity of the float member with the pivot is less than the specific gravity of the first fluid.

4. A differential float means according to claim 2 in which the pivot is located closer to one end of the float member than the other end so that in the presence of only the first fluid said one end of the float member pivots in a first direction, and in the presence of only the second fluid the said one end of the float member pivots in a direction opposite said first direction.

5. A differential float means according to claim 4 in which the specific gravity of said one end of the float member is substantially greater than the specific gravity of the other end for detecting entrainment of said first fluid in said second fluid.

6. A differential float means according to claim 5 in which the specific gravity of said one end of the float member is approximately 7.0 and the specific gravity of the other end is approximately 1.2.

7. A differential float means according to claim 6 in which the float member is formed of solid material substantially unaffected by the fluids in which it is to operate.

8. A sensor means for sensing the entrainment of a first fluid in a second fluid, the second fluid having a greater specific gravity than the first fluid, the sensing means comprising:

a chamber disposed upwardly for communication with the fluids; and, a differential float means having a float member shaped for location and movement within the chamber the float member having a specific gravity greater than those of the first and second fluids, whereby, in use, the first fluid can displace the second fluid from the chamber to inhibit buoying of the float member so that the float member is moved under the influence of said second fluid between two locations depending upon the buoying force exerted by the relative quantities of said fluids present for sensing the entrainment of the first fluid in the second fluid.

9. A sensor means according to claim 8 in which the differential float means also has a pivot, the float member being elongate and the pivot being located intermediate the length of the float member such that one end of the float member effects a counterbalance force which partially counterbalances the other end of the float member, whereby, in use, the float member is pivotable between said two locations under the influence of said fluids depending upon the buoying force exerted by the relative quantities of said fluids present in the chamber and whereby the pivoting of the float member depends upon the difference in pivoting force due to the buoying force of said fluids present plus the counterbalance force and the counter pivoting force of the other end of the float member.

10. A sensor means according to claim 8 also having an alarm means located for actuation by movement of the float member between the two locations.

11. A sensor means according to claim 8 in which the chamber has an inlet connected into a fluid line to allow fluid from the fluid line to flow into the chamber, the first fluid flowing into the chamber in preference to the second fluid.

12. A sensor means according to claim 11 in which the chamber has a bleed tube for allowing relatively slow flow of the first and second fluids out of the chamber back into the fluid line at a location downstream of the connection of the inlet into the fluid line, and a pressure reducing means located downstream of said inlet and upstream of the location in the fluid line at which the bleed tube returns the first and second fluids, the pressure reducing means reducing the pressure of said fluids downstream of the inlet for enabling flow of said fluid out of the chamber through the bleed tube back into the fluid line.

13. A sensor means according to claim 12 in which the bleed tube is a conventional restrictor tube.

14. A sensor means according to claim 12 in which the bleed tube is a restrictor having a groove formed in a piece of material, the groove being of irregular cross-section and having a plurality of bends whereby, in use, the irregularity of the cross-section and the number of bends in the groove increase the restriction created.

15. A sensor means according to claim 14 in which the groove is rectangular in cross-section.

16. A sensor means according to claim 15 in which the groove is about 1 mm deep and has a cross-section which is an isosceles triangle whose base has a length that is longer than the length of its sides.

17. A sensor means according to claim 14 in which the restrictor is removably attached to the chamber for allowing restrictors of differing restriction to be attached to the chamber.

* * * * *